(12) United States Patent
Spencer et al.

(10) Patent No.: US 9,066,513 B2
(45) Date of Patent: *Jun. 30, 2015

(54) METHOD FOR PREPARATION OF AN AQUEOUS GLYPHOSATE CONCENTRATE COMPOSITION HAVING MIXTURE OF AMINE SALTS

(75) Inventors: Allan Spencer, Ferntree Gully (AU); Aristos Panayi, Taylors Hill (AU); Chad Richard Ord Sayer, Brighton (AU)

(73) Assignee: Nufarm Australia Limited, Laverton North, Victoria (AU)

(*) Notice: Subject to any disclaimer, the term of this patent is extended or adjusted under 35 U.S.C. 154(b) by 0 days.

This patent is subject to a terminal disclaimer.

(21) Appl. No.: 13/876,913

(22) PCT Filed: Sep. 30, 2011

(86) PCT No.: PCT/AU2011/001251
§ 371 (c)(1),
(2), (4) Date: Jun. 27, 2013

(87) PCT Pub. No.: WO2012/040785
PCT Pub. Date: Apr. 5, 2012

(65) Prior Publication Data
US 2013/0281297 A1    Oct. 24, 2013

Related U.S. Application Data

(60) Provisional application No. 61/431,497, filed on Jan. 11, 2011, provisional application No. 61/388,670, filed on Oct. 1, 2010.

(51) Int. Cl.
*A01N 57/20* (2006.01)
*A01N 39/04* (2006.01)
*A01N 25/02* (2006.01)
*A01N 37/10* (2006.01)

(52) U.S. Cl.
CPC ............. *A01N 25/02* (2013.01); *A01N 57/20* (2013.01); *A01N 37/10* (2013.01); *A01N 39/04* (2013.01)

(58) Field of Classification Search
CPC ....... A01N 25/02; A01N 39/04; A01N 37/10; A01N 57/20
USPC .................................................. 504/127, 206
See application file for complete search history.

(56) References Cited

U.S. PATENT DOCUMENTS

| 6,455,473 | B2 | 9/2002 | Wright |
| 6,881,707 | B2 | 4/2005 | Howat et al. |
| 2006/0040826 | A1 | 2/2006 | Eaton et al. |
| 2006/0270556 | A1 | 11/2006 | Wright et al. |
| 2009/0062123 | A1 | 3/2009 | Quick et al. |

FOREIGN PATENT DOCUMENTS

| AU | 2007216730 B1 | 1/2009 |
| WO | WO 0126469 A1 * | 4/2001 |
| WO | 03013241 A1 | 2/2003 |
| WO | 2006023431 A2 | 2/2006 |
| WO | 2007143788 A1 | 12/2007 |
| WO | 2009075591 A1 | 6/2009 |
| WO | 2009154772 A2 | 12/2009 |

OTHER PUBLICATIONS

International Search Report for Corresponding International Application No. PCT/AU2011/001251 (mailed Nov. 3, 2011).
Search Report for GB1107525.6 (dated Sep. 28, 2011).
Search Report for GB1107540.5 (dated Sep. 28, 2011).

* cited by examiner

*Primary Examiner* — John Pak
*Assistant Examiner* — Andriae M Holt
(74) *Attorney, Agent, or Firm* — LeClairRyan, a Professional Corporation

(57) ABSTRACT

A method for preparing a glyphosate herbicidal aqueous concentrate to improve the handling of the concentrate, the method comprising forming a mixture of at least two nitrogen bases, and reacting the mixture of the at least two bases with glyphosate acid to provide an aqueous mixture of glyphosate salts wherein the concentration of glyphosate (based on glyphosate acid equivalent) is at least 200-gae/L.

18 Claims, 4 Drawing Sheets

METHOD FOR PREPARATION OF AN AQUEOUS GLYPHOSATE CONCENTRATE COMPOSITION HAVING MIXTURE OF AMINE SALTS

This application is a national stage application under 35 U.S.C. §371 of PCT Application No. PCT/AU2011/001251, filed Sep. 30, 2011, which claims the priority benefit of U.S. Provisional Patent Application Serial Nos. 61/388,670, filed Oct. 1, 2010, and 61/431,497, filed Jan. 11, 2011.

FIELD

The invention relates to a method of preparing the aqueous concentrate of glyphosate comprising a mixture of salts involving neutralizing glyphosate acid with a mixture of amine bases. The invention further relates to a method of transport and handling of aqueous glyphosate concentrates and the use of the aqueous concentrate in controlling plant growth.

BACKGROUND

Glyphosate is commonly used and distributed as an aqueous solution of a glyphosate salt such as the isopropyl ammonium, potassium or ammonium salts.

In order to reduce the transport and handling costs associated with glyphosate concentrates it is desirable to use a high loading of glyphosate, that is, the amount of active (usually expressed as glyphosate acid equivalent per liter of aqueous formulation) is desirably high within the bounds of the solubility and ability to conveniently pour and dilute the concentrate.

U.S. Pat. No. 6,544,930 (Wright) reports that high loadings can be achieved using the potassium salt of glyphosate and compositions of the potassium salt are available at loadings of 540 g acid equivalent (ae) per liter of aqueous formulation.

International Patent Publication No. WO 01/26469 discloses that aqueous formulations of glyphosate, including highly concentrated formulations, can be prepared using a mixture of glyphosate isopropyl amine and ammonium salts particularly in a weight ratio (expressed on a glyphosate a.e. basis) of 80:20 to 97:3.

U.S. Pat. No. 6,881,707 (Howat and Hay) reports a glyphosate composition comprising a mixture of salts of glyphosate comprising each of potassium and isopropylammonium salts. International Publication WO2006/023431 asserts that loadings of at least about 400 g glyphosate acid equivalent can be obtained by formulating in aqueous solution a mixture of salts of glyphosate at a total glyphosate a.e. concentration not less than about 360 gae/L, wherein (a) said glyphosate is in anionic form accompanied by low molecular weight non-amphiphilic cations in a total molar amount of about 100% to about 120% of the molar amount of said glyphosate; (b) said cations comprise potassium and propylammonium (e.g., IPA) cations in a mole ratio of about 70:30 to about 90:10; and (c) said potassium and propylammonium cations together constitute about 90 to 100 molar percent of all of said low molecular weight non-amphiphilic cations in the composition. The patent reports formulations of up to 590 g glyphosate acid equivalent per liter of aqueous formulation.

The concentrate formulation of glyphosate can be difficult to handle due to viscosity, particularly at low temperatures and high loadings of active. At high loadings the viscosity of the composition is increased to such an extent that it is often difficult to dispense the aqueous solution by pouring or pumping with normal pump equipment. Also the solution stability of the salts may be compromised, particularly at low temperatures so that precipitates form at low temperature which can not be readily resuspended or solubilised.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY

We provide a method for preparing a glyphosate herbicidal aqueous concentrate to improve the handling and stability thereof, the method comprising forming a mixture of at least two nitrogen bases and reacting the mixture of the at least two bases with glyphosate acid in an aqueous reaction medium to provide an aqueous mixture of glyphosate salts wherein the concentration of glyphosate (based on acid equivalent which is abbreviated as "ae") is at least 200 gae/L and preferably at least 360 gae/L.

The method uses a premix of nitrogen bases which is reacted with the glyphosate acid. The premix preferably comprises at least two nitrogen bases selected from the group consisting of ammonia, $C_1$ to $C_{10}$ alkylamine, di-($C_1$ to $C_6$ alkyl)amine, tri-($C_1$ to $C_6$ alkyl)amine, $C_1$ to $C_{10}$ alkanolamines, $C_1$ to $C_6$ alkyl($C_1$ to $C_6$ alkanol)amines and di-($C_1$ to $C_6$ alkyl)($C_1$ to $C_6$ alkanol)amines.

The concentration of glyphosate salts preferably is at least 450 gae/L, more preferably at least 500 gae/L. Still more preferably at least 550 gae/L and still more preferably 600 gae/L, such as at least 610 gae/L, at least 620 gae/L, at least 630 gae/L and at least 640 gae/L, at least 650 gae/L, at least 660 gae/L. In one preferred set of embodiments the loading of glyphosate is in the range of from 600 to 750 gae/L particularly 600 to 700 gae/L or up to the limits of solubility based on glyphosate acid equivalent.

In a preferred set of embodiments the nitrogen bases comprise at least two selected from the group consisting of ammonia, mono-($C_1$ to $C_8$) alkyl amines, di-($C_1$ to $C_6$) alkyl amines and tri-($C_1$ to $C_6$ alkyl) amines and more preferably from the group consisting of potassium hydroxide, ammonia, mono-($C_1$ to $C_6$) alkyl amines, di-($C_1$ to $C_6$) alkyl amines and tri-($C_1$ to $C_6$ alkyl) amines.

Throughout the description and the claims of this specification the word "comprise" and variations of the word, such as "comprising" and "comprises" is not intended to exclude other additives, components, integers or steps.

The reference to gae/L herein means grams of acid equivalent of the herbicide or salt. That is, the concentration is based on the mass of acid equivalent of the herbicide per liter of composition.

DETAILED DESCRIPTION

The method comprises forming a mixture, i.e. a premix, of nitrogen bases and combining the mixture of nitrogen bases with glyphosate acid.

The nitrogen bases may be selected from a range of compounds such as those of formula I:

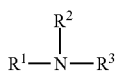

wherein:
R$^1$ is selected from the group consisting of hydrogen, C$_1$ to C$_{10}$ alkyl, C$_1$ to C$_{10}$ alkanol and C$_1$ to C$_{10}$ amino alkyl;
R$^2$ and R$^3$ are independently selected from the group consisting of hydrogen, C$_1$ to C$_6$ alkyl, C$_1$ to C$_6$ alkanol, C$_1$ to C$_6$ amino alkyl and the group wherein R$^2$ and R$^3$ together complete a 5 or 6 numbered heterocyclic ring containing the nitrogen in formula I and optionally a further heteroatom selected from O and N as a ring member and optionally substituted by C$_1$ to C$_6$ alkyl. Examples of compounds of formula I in which R2 and R3 complete a heterocyclic ring include piperazine, morpholine and the N-alkyl derivatives thereof.

The mixture of nitrogen bases will preferably contain at least two selected from the group consisting of ammonia, C$_1$ to C$_{10}$ alkylamine, di-(C$_1$ to C$_6$ alkyl)amine, tri-(C$_1$ to C$_6$ alkyl)amine, C$_1$ to C$_{10}$ alkanolamine C$_1$ to C$_6$ alkyl(C$_1$ to C$_6$ alkanol)amines and di-(C$_1$ to C$_6$ alkyl)(C$_1$ to C$_6$ alkanol)amines.

The mixture of nitrogen bases, in one set of embodiments contains at least two selected from the group consisting of ammonia, C$_1$ to C$_{10}$ alkylamine, di-(C$_1$ to C$_4$ alkyl)amine, tri-(C$_1$ to C$_4$ alkyl)amine, C$_1$ to C$_{10}$ alkanolamine C$_1$ to C$_4$ alkyl(C$_1$ to C$_4$ alkanol)amines and di-(C$_1$ to C$_4$ alkyl)(C$_1$ to C$_4$ alkanol)amines.

Specific examples of readily available nitrogen bases include those selected from the group consisting of ammonia, methylamine, dimethylamine, trimethylamine, ethylamine, diethylamine, triethylamine, propylamine, dipropylamine, tripropylamine, isopropylamine, diisopropylamine, butylamine, dibutylamine, tributylamine, isobutylamine, diisobutylamine, triisobutylamine, 1-methylpropylamine (D,L), bis (1-methyl)propylamine (D,L), 1,1-dimethylethylamine, pentylamine, dipentylamine, tripentylamine, 2-pentylamine, 3-pentylamine, 2-methylbutylamine, 3-methylbutylamine, bis(3-methylbutyl)amine and tris(3-methylbutyl)amine.

Specific examples of the preferred nitrogen bases may be selected from the group consisting of ammonia, methylamine, isopropylamine, dimethylamine, diethylamine, diisopropylamine, triethylamine and triisopropylamine.

In one set of embodiments the mixture of bases include at least one base other than ammonia and isopropylamine.

It is preferred that at least one of the nitrogen bases in the premix is a non-oxygen containing base such as those bases composed of nitrogen and at least one of nitrogen and hydrogen. Thus it is preferred at least one base of the premix is selected from the group consisting of ammonia, C$_1$ to C$_{10}$ alkylamine, di-(C$_1$ to C$_4$ alkyl)amine and tri-(C$_1$ to C$_4$ alkyl) amine. Specific examples of such bases include ammonia, methylamine, isopropylamine, dimethylamine, diethylamine, diisopropylamine, trimethylamine triethylamine and triisopropylamine.

The mixture of bases can have a wide range of base ratios. The mixture of the nitrogen bases will preferably comprise at least 3% by weight (preferably at least 5% and more preferably at least 10% up to 90%) by weight of each of at least two nitrogen bases based on the total weight of said nitrogen bases.

For example, in one embodiment there is from 5% to 95% by weight of each of two nitrogen bases. Further bases, for example a third and optionally a fourth nitrogen base may be present in smaller amounts or in amounts in this range of 5% to 95% if desired. In one embodiment there are two nitrogen bases in a weight ratio in the range of from 10:90 to 90:10 such as from 20:80 to 80:20.

Some of the amines are volatile and in these circumstances it may be preferred to introduce the volatile amine to a less volatile amine or to form a mixture of amines in a suitable solvent. In this embodiment the efficiency of the method is generally significantly improved when compared with conventional processes as the loss of volatiles is significantly reduced thereby reducing costs and the problem of volatile emissions which are particularly problematic in industrial scale exothermic reactions such as the reaction of bases with glyphosate. Volatility is a potential issue in exothermic conditions for amines of boiling point up to 80° C. and in particular up to 60° C. such as up to 50° C. or up to 40° C. In the case of bases which are gaseous at room temperature such as ammonia and methylamine dissolution in a liquid nitrogen base optionally in the presence of a diluent such as water can improve significantly the efficiency with which the bases react with glyphosate acid.

The mixture of nitrogen bases forms a premix composition, that is a mixture composition formed before mixing with the glyphosate acid. The premix is preferably a homogeneous mixture of the at least two nitrogen bases when it is added to the glyphosate acid.

Further bases and/or nitrogen containing adjuvants may be added to the compositions before or following the combination of the premix and glyphosate acid however the stoichiometry is preferably controlled to provide reaction of the base premix with at least the 50%, more preferably at least 80% and most preferably at least 90% of the glyphosate acid.

The glyphosate acid composition which is combined with the base premix may be in the form of a solid or may comprise a liquid. In one set of embodiments the glyphosate is a neat dry solid when combined with the base premix. In one embodiment the glyphosate acid is in the form of a solution in a suitable solvent for the glyphosate acid.

In one preferred set of embodiment the glyphosate acid composition combined with the nitrogen base premix comprises water. Glyphosate acid is conveniently manufactured in the form of a wetcake comprising glyphosate acid and residual water from the manufacturing process. The glyphosate acid used in the method may be the wetcake containing glyphosate. Typically the wetcake composition comprises, for example, at least 50% glyphosate such as at least 60%, at least 70% or at least 80% glyphosate. In one embodiment the glyphosate is in the form of a slurry containing glyphosate acid in particulate form and sufficient water to facilitate mixing and promote efficient reaction on combination with the base premix.

The method may involve addition of the base premix to glyphosate or addition of glyphosate to the premix. The two compositions, the base premix and glyphosate acid composition may also be simultaneously introduced to a reaction vessel. Generally addition of the base premix to glyphosate is preferred.

In a preferred set of embodiments the bases are added to the glyphosate acid aqueous composition in a mole ratio of bases: glyphosate acid in the range of from 0.9 to 1.3, preferably 0.9 to 1.2, more preferably 0.9 to 1.13 and still more preferably 1.0 to 1.1.

The reaction between the glyphosate acid and nitrogen bases may be carried out at a range of temperatures such as from 5° C. to 90° C. and preferably from 5° C. to 60° C.

The mixture of bases may be added in a single addition, stepwise and may be added quickly or over a period of time. In some cases, particularly if the glyphosate is neat or in very concentrated mixture such as a solid in a liquid such as a wetcake, suspension or slurry, there may be a significant exothermic reaction so that it may be appropriate to add the bases more slowly or to cool the reaction mixture. The composition of the mixture of bases may comprise a carrier such as water or other suitable liquid carrier to improve or vary the miscibility of the different bases. The presence of a carrier may also be used to regulate the rate of addition and/or the homogeneity of mixing with the glyphosate acid.

The composition and method may utilize more than two bases such as three, four or five bases but typically the use of two or three is convenient. When used the bases in addition to the two nitrogen bases may be nitrogen bases and/or non-nitrogen bases such as alkali metal bases.

In one set of embodiments the mixture of bases include an alkali metal hydroxide such as at least one of potassium hydroxide and sodium hydroxide. Potassium hydroxide is the most preferred alkali metal base.

On completion of the reaction the composition is a solution of the glyphosate in the form of a mixture of salts having a mixture of amine bases in the form of counter ions, which are generally cations, following neutralization of the glyphosate acid.

In general we have found that the viscosity of the aqueous glyphosate composition prepared by the process involving mixing the nitrogen bases to form a premix of bases prior to reaction with glyphosate acid has a significantly lower viscosity than the corresponding composition formed by reacting each of the nitrogen bases in sequence with glyphosate acid or from mixing the glyphosate salts formed with the corresponding nitrogen base counter ions. The method also allows base combinations to be prepared which would not otherwise be available, for example because of high viscosity or poor stability, if bases were added sequentially rather than as a premix.

The composition is prepared by mixing the composition comprising the premix of nitrogen bases with glyphosate acid. The concentration of the glyphosate acid will typically be at least 600 gae/L per liter of aqueous composition. The concentration of the glyphosate acid is preferably at least 610 gae/L preferably at least 620 gae/L, more preferably at least 630 gae/L and still more preferably at least 640 gae/L and most preferably at least 650 gae/L such as at least 650 gae/L at least 700 gae/L and at least 750 gae/L and up to the limit of solubility of the salts. The optimum concentration of the acid composition will of course depend on the nature of the nitrogen bases, their concentration and reaction conditions.

The method provides a significant advantage in the transport and handling of glyphosate concentrate. The ability to reduce significantly the viscosity of concentrates of a given loading or increase loading without the normal substantial increase in viscosity and consequential problems of instability handling has significant economic benefits for the manufacturer and farmer. The cost of transport of a given active glyphosate quantity can be reduced and/or more economic pumping or dispensing equipment can be used. Accordingly in one set of embodiments there is provided a method as hereinbefore described and further comprising loading the aqueous mixture of glyphosate salts into containers of volume in the range of 0.1 to 10000 liters to substantially fill the containers, transporting the filled containers and dispensing the aqueous mixture of glyphosate salts from the containers. The aqueous mixture of glyphosate salts is preferably pumped into the containers.

The glyphosate concentrate may and preferably will comprise a surfactant. The surfactant may be added at any time during the preparation process for example it may be present in the amine composition, in the glyphosate acid aqueous composition or may be added during and/or after reaction of the glyphosate acid with the mixture of amines. The appropriate method will depend on the chemical nature of the surfactant and amine reagent.

The method may be used in preparing glyphosate compositions containing adjuvants such as surfactants, antifoaming agents, stickers, penetrants or water conditioners like, pH adjusters, buffering agents & AMADS (monocarbamide dihydrogen sulfate i.e. urea+sulfuric acid), isethonic acid, sulphated glycerine, drift reduction agents and the like or may be used to prepare concentrates to which such adjuvants may be added during tank mixing. In one embodiment the method forms a concentrate used in a kit further comprising an adjuvant package comprising one or more adjuvants such as those selected from the group consisting of surfactants, antifoaming agents, stickers, penetrants, drift reduction agents and water conditioners such as those selected from the group consisting of pH adjusters, buffering agents & AMADS (monocarbamide dihydrogen sulfate i.e. urea+sulfuric acid), isethonic acid and sulphated glycerine, and the like.

Thus, in one set of embodiments there is provided a kit for controlling plant growth comprising a first part comprising the concentrate composition prepared by the method hereinbefore described and a second part comprising an adjuvant composition for mixing with the concentrate on dilution with water such as in a spray tank prior to application to plants to be controlled.

The dilute compositions for application to plants whose growth is to be controlled may be prepared on site by the end-user shortly before application to the foliage of vegetation to be controlled, by mixing in the glyphosate concentrate prepared in accordance with the above method with an aqueous diluent. The aqueous diluent may further comprise a surfactant such as one or more of those described above. Such compositions are generally referred to as "tank-mix" compositions.

In the case of a solution concentrate adapted for simple dilution prior to application the composition will preferably comprise a surfactant. In this set of embodiments the concentration of the surfactant may be up to 30% and preferably up to 20% by weight of the aqueous composition, such as in the range of from 0.1 to 20% by weight of the aqueous composition or from 1 to 15% by weight of the aqueous composition.

The surfactant may be present in the glyphosate acid composition prior to addition of the mixture of amines, it may be contained in the nitrogen base mixture added to the glyphosate acid, it may be mixed with the composition after the reaction or two or more of these addition strategies may be used. The appropriate mode of addition of the surfactant, when used, will depend on the nature of the surfactant. For example, some surfactants may be reactive with one or more of the acid or base components individually and it may be preferred to avoid such contact in those cases.

Amphiphilic agents which have been claimed to enhance the herbicidal efficacy of formulations comprising glyphosate salts include the following: quaternary ammonium surfactant; etheramine surfactants; alkylether and amine surfactant combinations; acetylenic diol and alkyl(poly)glycoside surfactant combinations; lipophilic fatty amine ethoxylate surfactants; alkoxylated amine surfactants; betaine surfactants; alkyl polyglycoside agents; secondary or tertiary alcohol surfactants; silicone copolymer wetting agents and trialkylamine oxide or quaternary amine or trialkylbetaine surfactant combinations; sorbitan fatty acid ester and amine, quaternary ammonium or alkylglycoside surfactant combinations; surfactants derived from alkanethiols; polyoxyalkylene trisiloxane surfactants; super-wetting agents such as silicone-based and fluorocarbon-based surfactants; supra-molecular aggregates comprising one or more amphiphilic salts having a glyphosate anion and cation derived by protonation of secondary or tertiary oily amines; alkoxylated primary alcohol surfactants; alkyl polysaccharide derivates; alkyl polyglycoside and ethoxylated alcohol combinations; alkylglucosides; surfactants comprising polyhydroxyhydrocarbyl and amine functionality; alkylglycoside and alkoxylated alkylamine surfactant combinations; alkyldiamine tetraalkoxylate surfactants; succinic acid derivatives; alkoxylated amido amines; sugar glycerides such as rapeseed oil sugar glyceride; diamine surfactants; widely-bridged alcohol polyethoxylates; water-soluble long-chain hydrocarbyl dimethylamine oxides and quaternary ammonium halide combinations; hydroxyalkylammonium adjuvants; polyether diamine surfactants; cationic, anionic, nonionic or zwitterionic silicone adjuvants; organosilicone surfactants and diphenyl oxide sulfonate surfactant combinations; a range of ether phosphate adjuvants; phosphourous surfactant adjuvants; polyglycerol and polyglycerol derivatives; $C_8$-$C_{22}$ sarcosinate or sarcosinate salts; ethoxylated vegetable oils; polyethoxylated dialkylamine surfactants; $C_{10}$-$C_{18}$ alkylpolyglycol ether sulfates; Sucrose & Sorbital Surfactants; Sorbitan Esters; Ethoxylated Saccahrose Esters; Coco Amido Propyl Dimethylamine Alkyldimethylamines; Phosphated Esters Tallow Amine Surfactants; Trisiloxanes; TEA and MDEA Esterquats; Dimethylethanolamine based Esterquats; Saccharides, such as Alkyl Polysaccharide as well a glucosides; Alkyl Polypentosides (APP); Polyglycerines; Etheramine Alkoxylates; Sorbitan Monolaurate; Pine Terpinic compounds such oligomers etc (derived from alpha pinene & beta pinene)/Pine Oils; Cocoamine ethoxylates; Acrylates & Latex compounds; (Ethoxylated) Oleyl Alcohols; Alkylamine Alkoxylates; Etheramine Alkoxylates/Alkyl Etheramine; Quaternary Ammonium Salts/Ammonium Quaternary Derivatives; Quat Amines; Amine Oxides; Dialkoxylates Amines; Alkyl Alkoxylated Phosphates; Aminated Alkoxylated Alcohols; Dialkoxylated Amines; Carboxylates; Alkylethersulfates; Disodium sulfosuccinates/Succinates; Polyether Amines; Cocoamidopropyl betaines and salts of fatty acids.

Etheramine surfactants include surfactants having the representative chemical structure (a)

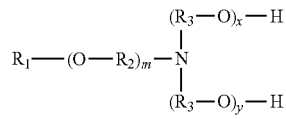

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$-$C_4$ alkylene, $R_3$ groups are independently $C_1$-$C_4$ alkylene, and x and y are average numbers such that x+y is in the range from 2 to about 60; or (b)

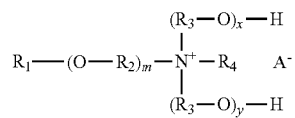

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$-$C_4$ alkylene, $R_3$ groups are independently $C_1$-$C_4$ alkylene, $R_4$ is $C_1$-$C_4$ alkyl, x and y are average numbers such that x+y is in the range from 0 to about 60 and $A^-$ is an agriculturally acceptable anion; or (c)

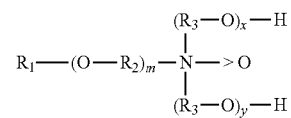

wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$-$C_4$ alkylene, $R_3$ groups are independently $C_1$-$C_4$ alkylene and x and y are average numbers such that x+y is in the range from 2 to about 60.

In one set of embodiments the glyphosate composition prepared by the method is substantially free of surfactants, prior to use, for example, when the concentrate is diluted with water in a spray tank prior to use.

In a further set of embodiments we provide a method for controlling plant growth comprising diluting the concentrate with water, optionally with addition of adjuvant, and applying the glyphosate to plants by, for example spray or application via a substrate on which the diluted composition is sorbed.

One of the important advantages of the glyphosate compositions prepared according to the method is that the glyphosate concentration can be increased to very high levels, for example even over 600 g a.e./L, yet the surfactant concentration may still be included in a concentrate adequate to give excellent herbicidal performance without the end-user requiring to add more surfactant in the spray tank. In many cases the compositions prepared by the methods allow incorporation of surfactant which would not otherwise be possible for corresponding compositions prepared by combination of preformed salts or compositions prepared by sequential neutralization of glyphosate acid with different bases. In other cases the compositions prepared by the method provides handling characteristics such as pourability and pumping performance superior to the corresponding compositions prepared by combination of preformed salts or compositions prepared by sequential neutralization of glyphosate acid with different bases. The aqueous concentrates also generally have remarkably good storage stability under a wide range of temperature conditions despite the high loading of glyphosate and are generally superior to corresponding compositions prepared by combination of preformed salts of monobases (i.e. a glyphosate salt prepared using a single base in a separate vessel) or compositions prepared by sequential neutralization of glyphosate acid with different bases.

Mixtures of glyphosate with other herbicides and pesticides may also be prepared from the concentrated prepared by the method described above. Examples of such other agrochemicals include glufosinate, 2,4-D, MCPA, dicamba, diphenylethers, imidazolinones, sulfonylureas, insecticides and fungicides.

In one embodiment the method further comprises forming a mixture of at least one further acid herbicide with glyphosate acid and reacting the mixture of the at least two bases with the mixture of glyphosate acid and at least one other acid herbicide to provide a mixture of glyphosate salts and a mixture of salts of said at least one further herbicidal acid. The further acid herbicide will preferably comprise at least one acid group selected from phosphonic acid, sulfonic acid and carboxylic acid and preferably at least one carboxylic acid group.

The at least one further herbicidal acid may be selected from the group consisting of:
 (i) benzoic acid herbicides such as acifluorfen chloramben; dicamba; 2,3,6-TBA; tricamba;
 (ii) pyrimidinyloxybenzoic acid herbicides such as bispyribac and pyriminobac; pyrimidinylthio-benzoic acid herbicides such as pyrithiobac;
 (iii) picolinic acid herbicides such as aminopyralid, clopyralid and picloram;
 (iv) quinolinecarboxylic acid herbicides such as quinclorac and quinmerac;
 (v) phenoxy acid herbicides such as 4-CPA, 2,4-D, 3,4-DA, MCPA and 2,4,5-T;
 (vi) phenoxybutyric herbicides such as 4-CPB, 2,4-DB, 3,4-DB, MCPB and 2,4,5-TB;
 (vii) phenoxypropionic herbicides such as cloprop, 4-CPP, dichlorprop, dechlorprop-P, fenoprop, mecoprop, mecoprop-P;
 (viii) acid substituted diphenyl ether herbicide such as ethoxyfen;
 (ix) aryloxy phonoxypropionic acid herbicides such as chlorazifop, clodinafop, clofop, flueroglycofen, cyhalofop, diclopfop, fenoxaprop, fenoxaprop-P, fenthiaprop, fluazifop, fheazifoop-P, haloxyfop, haloxyfop-P, isoxapyrifop, metamifop, propaquizafop, quizalofop, quizalofop-P and trifop;
 (x) herbicides such as benzoylprop, aryalamine, flamprop and flamprop-M;
 (xi) acid substituted nitro phenyl ether herbicides such as acifluorfen; and
 (xii) organophosphorous herbicides other than glyphosate such as glufosinate and glufosinate-P.

The more preferred acid herbicides for use in the invention are selected from the group consisting of dicamba, aminopyralid, clopyralid, picloram, 2,4-D, MCPA, 2,4-DB, mecaprop, mecoprop-P, glufosinate, diclofop and fluazifop. Still more preferably, the one or more further acid herbicides when used with glyphosate acid are selected from the group consisting of dicamba, clopyralid, 2,4-D, MCPA and mecoprop.

It is preferred where there are a mixture of acid herbicides that the concentration of glyphosate in the final concentrate is at least 200 gae/L (preferably at least 360 gae/L, more preferably at least 450 gae/L) and that the total acid herbicide salts (including glyphosate) in the final composition is at least 360 gae/L, more preferably at least 450 gae/L, still more preferably at least 550 gae/L and most preferably at least 600 gae/L.

When further acid herbicides are used in the process of the invention the glyphosate will typically comprise at least 20% by weight based on acid equivalent of the total acid herbicides, preferably glyphosate acid will constitute at least 40% by weight, still more preferably at least 60% by weight and most preferably at least 80% by weight of the total acid herbicides including glyphosate.

In one embodiment, the glyphosate acid constitutes at least 95% more preferably at least 98% of the total acid herbicides (including glyphosate).

In a further embodiment, the glyphosate composition mixed with the mixture of at least two nitrogen bases is free of other herbicidal acids.

In the embodiments in which a mixture of acid herbicides including glyphosate are reacted with the mixture of at least two nitrogen bases it is preferred that the molar ratio of total nitrogen bases:total acid herbicides is in the range of 0.9:1 to 1.3:1.

Methods of use of glyphosate formulations are well known to those of skill in the art. Aqueous concentrate compositions prepared by the method may be diluted in an appropriate volume of water and applied, for example by spraying, to unwanted vegetation to be controlled. Compositions prepared by the method may be applied at glyphosate a.e. rates in the range of for example from about 0.1 to about 5 kilograms per hectare (kg/ha), occasionally more. Typical glyphosate a.e. rates for control of annual and perennial grasses and broadleaves are in the range from about 0.3 to about 3 kg/ha. Compositions of the invention may be applied in any convenient volume of water, most typically in the range from about 30 to about 2000 liters per hectare (l/ha). Compositions prepared by the method of the invention also include solutions which may be applied by spraying for example. In these solutions, the concentration of glyphosate is selected according to the volume per unit area of spray solution to be used and the desired rate of application of glyphosate per unit area. For example, conventional spraying is done at 30 to 5000 liters (particularly 50-600 liters) of spray solution per hectare, and the rate of application of glyphosate is typically 0.125 to 1.5 kg of glyphosate acid equivalent per hectare. Spray solution compositions can be prepared by diluting the aqueous liquid concentrates preferably comprising surfactant adjuvants or by tank mixing the aqueous concentrates formed by the method with adjuvants as described above.

The invention will now be described with reference to the following examples. It is to be understood that the examples are provided by way of illustration of the invention and that they are in no way limiting to the scope of the invention.

EXAMPLES

The Examples are described in part with reference to the drawings. In the drawings.

Figure 1:
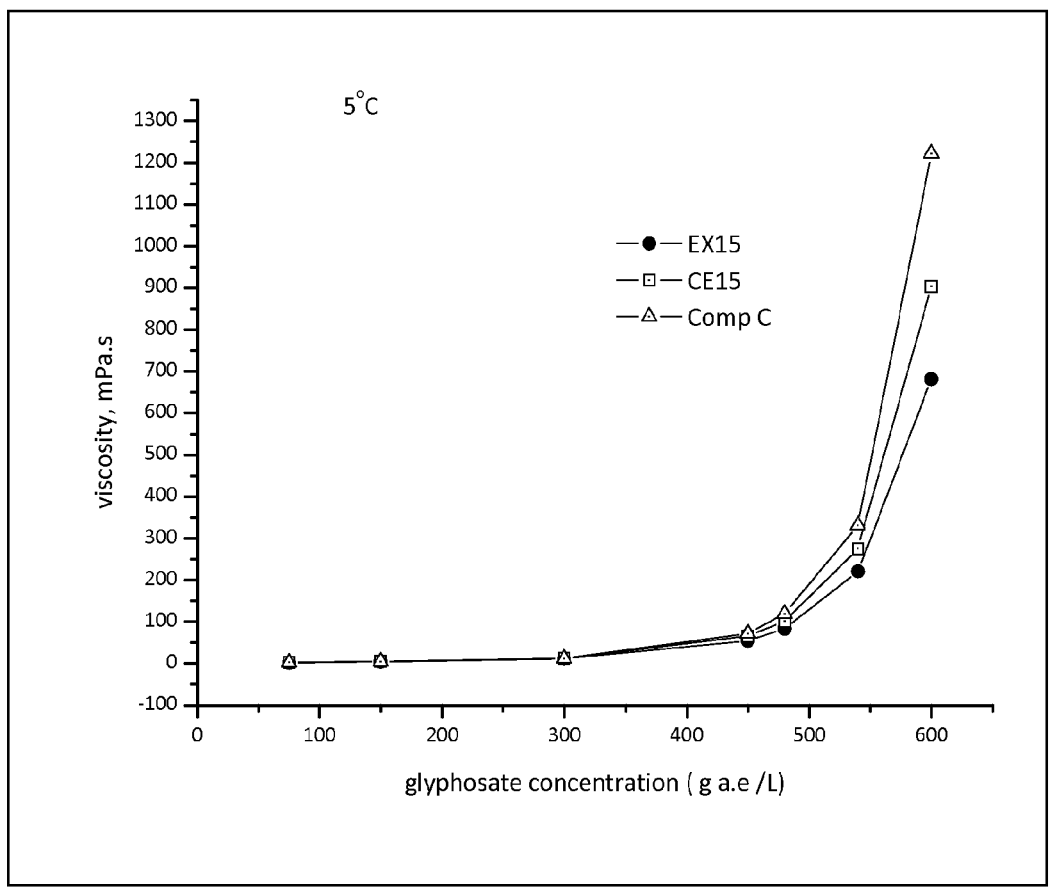
FIG. 1 is a graph showing the change in viscosity with concentration for Composition Example 14 and Comparative Example 14 and Control Composition C at 5° C.

The following abbreviations are used for the bases which are used to form glyphosate counter ions:
 MMA—monomethylamine
 MIPA—monoisopropylamine
 NH3—ammonia
 TEA—triethylamine
 KOH—potassium hydroxide
 NaOH—sodium hydroxide
 MEA—monoethanolamine DMA—dimethylamine In the Examples pH was determined by the method described in CIPAC MT_75.3 at 5% w/V in deionised water. Viscosity was determined at 5° C. and at 20° C.

The viscosity of compositions was measured after equilibrating the composition at the respective temperatures using a Brookfield viscometer (model DV-1) Spindle 21 in a fixed volume temperature controlled cylinder to ensure direct comparability.

Examples (E) 1 to 13 and Comparative Examples (CE) 1 to 13 and Comparative Example C Compositions of glyphosate salts were prepared from glyphosate acid using the nitrogen bases added in accordance with (A) a process in accordance with the invention in which the bases were premixed and the premix of bases added to an aqueous slurry of glyphosate acid; and (B) a comparative process in which bases were reacted with glyphosate acid by separate addition of the bases in sequence.

(A) In the premixed addition process the bases shown in the table were mixed in the molar ratios indicated and were added to an aqueous slurry of glyphosate acid in an amount to neutralise the glyphosate acid (equimolar amount). Where indicated in the table a surfactant was used and was added to the composition following neutralisation of the glyphosate acid. The final composition had a glyphosate concentration based on glyphosate acid equivalent indicated in the table expressed in grams of glyphosate acid equivalent per liter of composition (gae/l Glyphosate).

(B) In the separate addition process the bases identified in the table were separately added in sequence in the molar base ratio identified in the Table to an aqueous slurry of glyphosate acid in an amount to neutralise the glyphosate acid. Where indicated in the table a surfactant was used and was added to the composition following neutralisation of the glyphosate acid. The final composition had a glyphosate concentration based on glyphosate acid equivalent indicated in the table expressed in grams of glyphosate acid equivalent per liter of composition (gae/l Glyphosate).

(C) For Example "CEC13", the monobase mixture was also prepared by mixing preformed individual salts in water. That is, the preformed MEA salt of glyphosate and the preformed MIPA salt of glyphosate were mixed in the molar ratio shown.

TABLE 1

| Example | base | base ratio | Base addition process | gae/L Glyphosate | Surfactant | g/L Surfactant | 5% pH | Viscosity 5° C. (mPa · s) | Viscosity 20° C. (mPa · s) | 1 to 7 to more days later |
|---|---|---|---|---|---|---|---|---|---|---|
| 1 | MMA/MIPA/NH3 | 70/25/5 | premix | 600 | Surf. A | 140 | 4.61 | 742 | 256 | |
| CE1 | MMA/MIPA/NH3 | 70/25/5 | separate | 600 | Surf. A | 140 | 4.45 | 1340 | 402 | |
| 2 | MMA/MIPA/NH3 | 70/25/5 1:1.3 | premix | 600 | Surf. A | 140 | 5.11 | 1868 | 584 | |
| CE2 | MMA/MIPA/NH3 | 70/25/5 1:1.3 | separate | 600 | Surf. A | 140 | 5.07 | 3195 | 729 | |
| 3 | MMA/MIPA/NH3 | 70/25/5 | premix | 650 | None | 0 | 4.71 | 568.1 | 214.1 | |
| CE3 | MMA/MIPA/NH3 | 70/25/5 1:1.3 | separate | 650 | None | 0 | 5.42 | 1895 | 578 | |
| 4 | DMA/MIPA/NH3 | 70/25/5 | premix | 650 | Surf. B | 90 | 4.68 | 1318 | 468 | |
| CE4 | DMA/MIPA/NH3 | 70/25/5 | separate | 650 | Surf. B | 90 | 4.7 | 1623 | 472.5 | solidified |
| 5 | MMA/MIPA/KOH | 45/10/45 | premix | 650 | None | 0 | 4.5 | 312 | 143 | |
| CE5 | MMA/MIPA/KOH | 45/10/45 | separate | 650 | None | 0 | 4.49 | 328.4 | 146.7 | |
| 6 | TEA/MMA/NH3 | 10/80/10 | premix | 650 | Surf. A | 100 | 4.75 | 2734 | 1175 | |
| CE6 | TEA/MMA/NH3 | 10/80/10 | separate | 650 | Surf. A | 100 | 4.78 | 984 | 986 | gelled |
| 7 | MEA/MIPA/NH3 | 70/25/5 | premix | 600 | None | 0 | 4.35 | 466.2 | 178.5 | |
| CE7 | MEA/MIPA/NH3 | 70/25/5 | separate | 600 | None | 0 | 4.35 | 521.3 | 198.5 | precipitate |
| 8 | MEA/MIPA/NH3 | 70/25/5 | premix | 540 | Surf. A | 140 | 4.36 | 454.7 | 172.3 | |
| CE8 | MEA/MIPA/NH3 | 70/25/5 | separate | 540 | Surf. A | 140 | 4.35 | 499.9 | 194.3 | precipitate |
| 9 | MEA/MIPA | 70/30 | premix | 600 | None | 0 | 4.55 | 568.3 | 200.4 | |
| CE9 | MEA/MIPA | 70/30 | separate | 600 | None | 0 | 4.6 | 1022 | 317.8 | |
| 10 | MEA/MIPA | 70/30 | premix | 540 | Surf. A | 140 | 4.53 | 479.7 | 156.3 | |
| CE10 | MEA/MIPA | 70/30 | separate | 540 | Surf. A | 140 | 4.6 | 694.3 | 225.8 | |
| 11 | MMA/MIPA/KOH | 50/20/30 | premix | 650 | None | 0 | 4.4 | 332.8 | 139.7 | |
| CE11 | MMA/MIPA/KOH | 50/20/30 | separate | 650 | None | 0 | 4.51 | 401.1 | 155.7 | |
| 12 | MMA/MIPA/KOH | 50/20/30 | premix | 570 | Surf. A | 140 | 4.45 | 671.4 | 268.3 | |
| CE12 | MMA/MIPA/KOH | 50/20/30 | separate | 570 | Surf. A | 140 | 4.55 | 837.9 | 282 | |
| 13 | MEA/MIPA | 70/30 | premix | 600 | None | 0 | — | 681 | 217 | |
| CE 13 | MEA/MIPA | 70/30 | separate | 600 | None | 0 | — | 904 | 298 | |
| CEC 13 | MEA/MIPA | 70/30 | Monobase mixture | 600 | None | 0 | — | 1222 | 372 | |

Surf. A Quaternary amine surfactant
Surf. B Ternary surfactant blend of cationic, anionic and N-oxide surfactant
Surf. C Tallow amine surfactant blend Example 14

A composition (Example 14) was prepared in accordance with the general procedure of the invention containing 613 gae glyphosate per liter using the premixed ratio of bases set out below. The compositions of the invention were compared with a control "Roundup PowerMax" (Trademark of Monsanto) glyphosate product containing 540 gae glyphosate acid equivalent per liter of aqueous concentrate and an untreated control.

Samples of the compositions were each diluted to provide sub samples of concentrations 3.5 gae/L, 7.0 gae/L and 10.5 gae/L which were applied to plants sown 7 days before treatment. Application details are as follows:

Test Species
Oats (*Avena sativa* var *Echidna*)
Variegated Thistle (*Silybum marianum*)

Plant Growth Stage when Herbicide Applied
Oats 2-2.2 leaf (sprayed 20 days after sowing)
Variegated Thistle 8-17 cm rosette (sprayed 28 days after sowing)
Trial replicates 6
Applied in a total application volume of 145 L/ha
Applied in enclosed laboratory track sprayer with 110o flat fan nozzle (Teejet XR11001-VS) at 100 kPa Materials and Methods 1.1 Plant Propagation Oat seeds were sown to 4 cm depth and variegated thistle was sown to 1 cm depth in 10 cm diameter pots filled with potting mix (AS 3743). One week after seedling emergence, seedlings were thinned for uniform size to one seedling per pot. Oats were grown in a temperature-controlled greenhouse (14 C-25 C) for 8 days then outdoors for 12 days prior to spray application, to more closely simulate field conditions. Variegated thistle was grown in a temperature-controlled greenhouse (14 C-25 C) for 16 days then outdoors for 12 days prior to spray application. After the application of herbicides the pots were returned to the greenhouse until harvested for fresh weight.

1.2 Herbicide Application

Herbicide formulations were applied using an enclosed laboratory track-sprayer fitted with a 110° flat fan nozzle (Teejet XR11001-VS), at a pressure of 100 kPa applying a spray volume of 145 L/ha.

1.3 Assessments

Visual observations of % biomass and % brownout were recorded. Seedlings were harvested by cutting foliage off at base immediately prior to weighing on a Sartorius Basic electronic balance (range 0-4100 g) 14DAT.

Fresh weights (g) of weed were determined 14 days after treatment and an average of six replicates is reported in Tables 2a and 2b for Variegated Thistle and Oats respectively. The biomass as a percentage of untreated control is reported in Tables 2c and 2d for Variegated Thistle and Oats respectively.

TABLE 2a

Freshweight (g) of Variegated Thistle: 14-days after treatment

| | Glyphosate Applied | | |
|---|---|---|---|
| | 3.5 gae/L | 7 gae/L | 10.5 gae/L |
| Control Roundup PowerMax (540 gae/L K salt) | 1.4 | 0.64 | 0.77 |
| Example 14: 613 gae/L Glyphosate as 70% MMA, 25% MIPA, 5% NH3 and 150 g/L Surf. C | 1.3 | 0.58 | 0.59 |

Untreated Control results—The variegated Thistle untreated control results were (3 treatments replicated six times) 14.65 g, 13.53 g & 13.24 g (average 13.81 g).

TABLE 2b

Freshweight (g) of Common Oats: 14-days after treatment

| | Glyphosate Applied | | |
|---|---|---|---|
| | 3.5 gae/L | 7 gae/L | 10.5 gae/L |
| Control Roundup PowerMax (540 gae/L K salt) | 0.28 | 0.25 | 0.2 |
| Example 14: 613 gae/L Glyphosate as 70% MMA, 25% MIPA, 5% NH3 and 150 g/L Surf. C | 0.35 | 0.29 | 0.29 |

Untreated Control for Common Oats provided freshweights (3 treatments replicated six times) of 2.29 g, 2.58 g and 2.35 g (average 2.40 g)

TABLE 2c

Biomass (% of untreated control) of Variegated Thistle: 10-days after treatment

| | Glyphosate Applied | | |
|---|---|---|---|
| | 3.5 gae/L | 7 gae/L | 10.5 gae/L |
| Control Roundup PowerMax (540 gae/L K salt) | 27 | 18 | 22 |
| Example 14: 613 gae/L Glyphosate as 70% MMA, 25% MIPA, 5% NH3 and 150 g/L Surf. C | 23 | 15 | 13 |

Untreated Control results—The variegated Thistle untreated control results were (3 treatments replicated six times) 14.65 g, 13.53 g & 13.24 g (average 13.81 g).

TABLE 2d

Biomass (% of untreated control) of Common Oats: 9-days after treatment

| | Glyphosate Applied | | |
|---|---|---|---|
| | 3.5 gae/L | 7 gae/L | 10.5 gae/L |
| Control Roundup PowerMax (540 gae/L K salt) | 50 | 45 | 48 |
| Example 14: 613 gae/L Glyphosate as 70% MMA, 25% MIPA, 5% NH3 and 150 g/L Surf. C | 50 | 50 | 48 |

Untreated Control for Common Oats provided fresh weights (3 treatments replicated six times) of 2.29 g, 2.58 g and 2.35 g (average 2.40 g)

Example 15

Viscosity/Conductivity Dilution Experiments

To further compare the compositions prepared by the method of the invention with corresponding mixtures prepared by other methods. The compositions Example 13, CE 13 and CEC13 of Table 1 were diluted and their viscosity and conductivity measured and the results compared.

Example 15 (premixed) refers to the range of dilutions prepared from Ex 13 and the results are shown in Table 3a; CE 15 (separate) refers to the range of dilutions prepared from CE 13 and the results are shown in Table 3b, and Comp C (Monobase mix) refers to the range of dilutions prepared from CEC13 of Table 1, and these results are shown in Table 3c. These batches were mixed for 10 minutes following dilution and the conductivity and viscosity at 5° C. and 20° C. (spindle 21) was measured.

TABLE 3a

Ex 15 MEA/MIPA 70/30

| Sample | Glyphosate gae/L | Viscosity 5° C. (mPa·s) | Viscosity 20° C. (mPa·s) | Ms/cm Conductivity | Temp ° C. |
|---|---|---|---|---|---|
| | 600 | 681 | 217 | 3.01 | 26 |
| | 540 | 220.5 | 77.3 | 6.01 | 26 |
| | 480 | 83 | 36.4 | 10.4 | 26 |

TABLE 3a-continued

Ex 15 MEA/MIPA 70/30

| Sample | Glyphosate gae/L | Viscosity 5° C. (mPa·s) | Viscosity 20° C. (mPa·s) | Ms/cm Conductivity | Temp ° C. |
|---|---|---|---|---|---|
| | 450 | 54.5 | 26.3 | 11.8 | 26 |
| | 300 | 11 | 6.5 | 25.4 | 26 |
| | 150 | 4 | 2.9 | 28.1 | 26 |
| | 75 | 2 | 1.4 | 19.5 | 26 |

TABLE 3b

CE 15 MEA/MIPA 70/30

| Sample | Glyphosate gae/L | Viscosity 5° C. (mPa·s) | Viscosity 20° C. (mPa·s) | Ms/cm Conductivity | Temp ° C. |
|---|---|---|---|---|---|
| | 600 | 904 | 298 | 2.8 | 26 |
| | 540 | 275 | 104.5 | 5 | 26 |
| | 480 | 101 | 46.8 | 8.85 | 26 |
| | 450 | 65.6 | 31 | 11.53 | 26 |
| | 300 | 12 | 7.1 | 24.5 | 26 |
| | 150 | 5 | 4.2 | 27.1 | 26 |
| | 75 | 2.7 | 1.4 | 19.27 | 26 |

TABLE 3c

Comp C (Monobases g/h 70/30)

| Sample | Glyphosate gae/L | Viscosity 5° C. (mPa·s) | Viscosity 20° C. (mPa·s) | Ms/cm Conductivity | Temp ° C. |
|---|---|---|---|---|---|
| | 600 | 1,222 | 372 | 2.08 | 26 |
| | 540 | 332 | 124.4 | 4.62 | 26 |
| | 480 | 119 | 54.2 | 8.1 | 26 |
| | 450 | 72.3 | 33.5 | 10.6 | 26 |
| | 300 | 12.1 | 7.5 | 23.9 | 26 |
| | 150 | 4 | 2.7 | 27 | 26 |
| | 75 | 2.7 | 1.8 | 19.02 | 26 |

Figure 2:
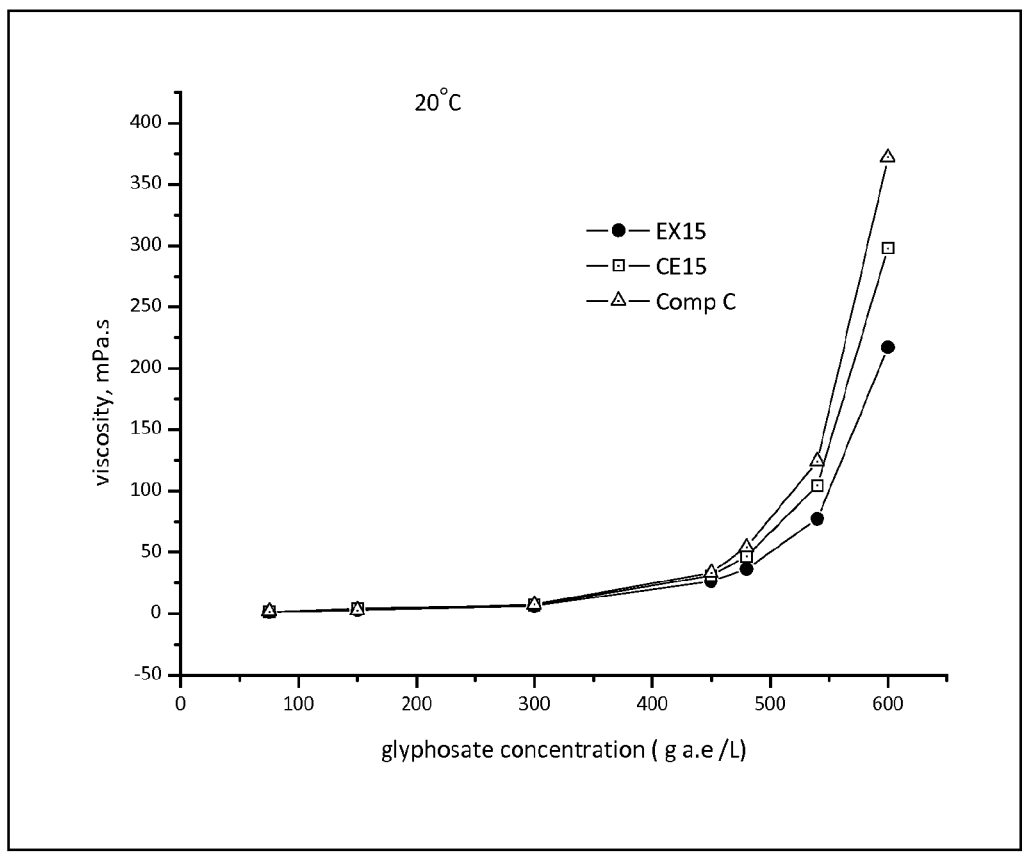
FIG. 2 is a graph showing the change in viscosity with concentration for Composition Example 14 and Comparative Example 14 and Control Composition C at 20° C.

The viscosity results are plotted for in three plots for Ex 15, CE 15 and Comp C in graphs for measurements at 5° C. and 20° C. in FIGS. 1 and 2 respectively. The results show that the differences decrease at lower concentrations but are very significant at higher loadings. The compositions of the invention formed from premixed base have a lower viscosity than the separate bases batch which in turn has a lower viscosity than the monobase mixed batch.

Figure 3:
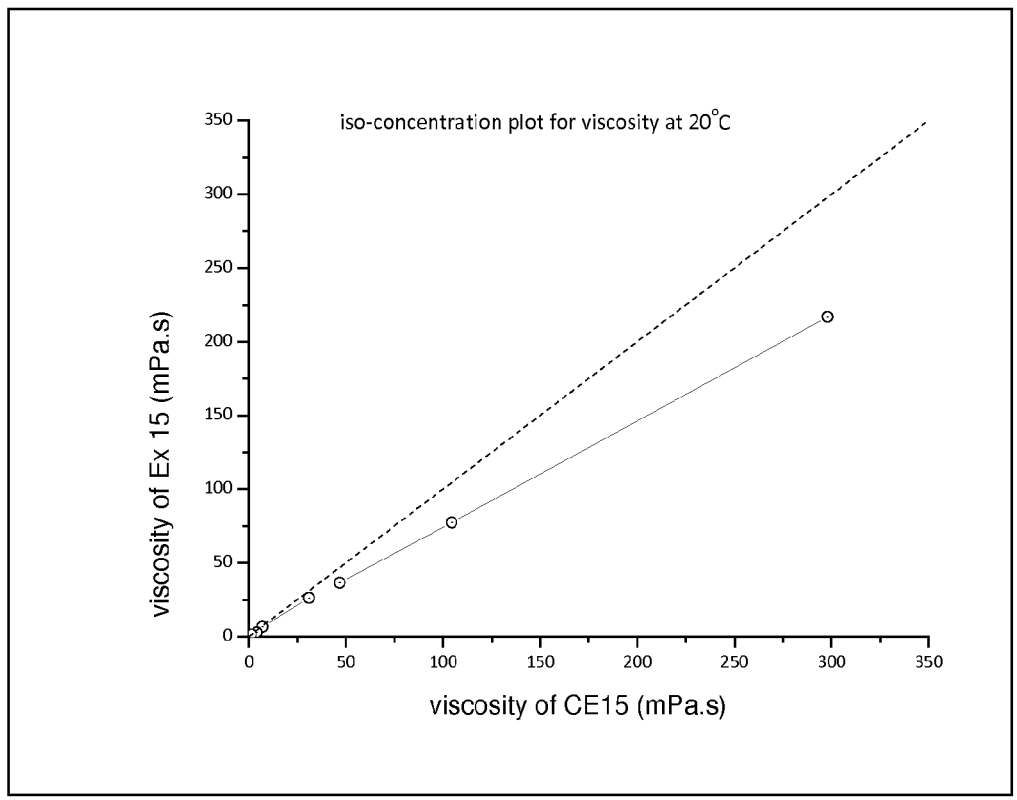
FIG. 3 is an isoconcentration plot of conductivity for Composition Example 14 and Comparative Example 14 at 20° C.
Figure 4:
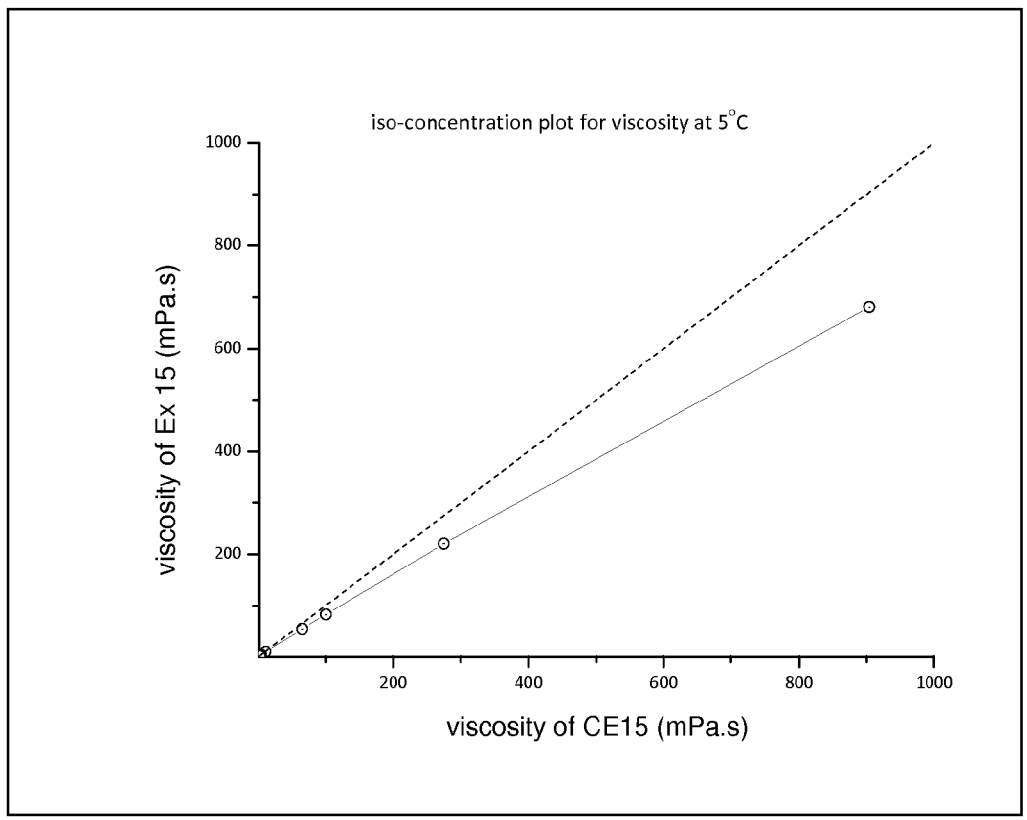
FIG. 4 is an isoconcentration plot of conductivity for Composition Example 14 and Comparative Example 14 at 5° C.

The conductivity results are plotted in iso-concentration graphs of Ex 15 and CE 15 with results at 5° C. and 20° C. being in FIGS. 3 and 4 respectively.

The composition formed by the method of the invention from premixed bases has a higher conductivity than the corresponding composition formed from separate bases batch which in turn has a higher conductivity than the corresponding composition formed from mixed monobases. This confirms the viscosity results and the differences between batches using the three different methods of manufacture.

Example 16

This example demonstrates the method of the invention in which a mixture of glyphosate acid and a further acid herbicide is neutralised with a mixture of nitrogen containing bases.

Composition comprising a mixture of glyphosate salts 200 gae/L and a mixture of 2,4-D salts, 200 gae/L, were prepared (a) in Example 16 in accordance with the invention in which an aqueous mixture of glyphosate acid and 2,4-D acid each at 200 g/L based on the final concentration was neutralised with a premix of DMA/MMA in an 80/20 mole ratio; (b) in comparative examples 16a to 16d by separate mixing of bases with the herbicide acid mixture or separate herbicide as shown in Table 4. Viscosity of the final concentrate is shown in Table 4.

TABLE 4

| Example No. | g/L Glyphosate | g/L 2,4D | Base Mixing | Bases | 80/20 | Viscosity 5° C. cp | Viscosity 20° C. cp | Appearance | SG | pH |
|---|---|---|---|---|---|---|---|---|---|---|
| 16 | 200 | 200 | Premix | DMA/MMA | 80/20 | 26.6 | 13.2 | Clear sol | 1.164 | 9.02 |
| CE16a | 200 | 200 | Separate | DMA/MMA | 80/20 | 36.5 | 16.5 | Clear sol | 1.163 | 9.7 |
| CE16b | 200 | 200 | Separate | DMA/MMA | 80/20 | 38.8 | 18.5 | Clear sol | 1.162 | 9.8 |
| CE16c | | 400 | Separate | DMA/MMA | 80/20 | 14.8 | 8.3 | Clear sol | 1.133 | 10 |
| CE16d | 400 | | Separate | DMA/MMS | 80/20 | 115.8 | 47.3 | Clear sol | 1.174 | 9.7 |

The results show the significant reduction in viscosity from neutralization of the herbicidal acids with a preformed mixture of bases when compared with the corresponding composition formed by mixing two compositions of the herbicidal acids each neutralized with one of the bases. This difference in viscosity is significant even though the two concentrate compositions are equivalent (see Ex 16 and CE16a).

The invention claimed is:

1. A method for preparing a glyphosate herbicidal aqueous concentrate to improve the handling of the concentrate, the method comprising: forming a mixture of at least two nitrogen bases, and reacting the mixture of the at least two bases with glyphosate acid to provide an aqueous solution comprising a mixture of glyphosate salts wherein the concentration of glyphosate (based on glyphosate acid equivalent) is at least 500 gae/L, wherein the at least two nitrogen bases are selected from the group consisting of ammonia, $C_1$ to $C_{10}$alkylamine, di-($C_1$ to $C_6$ alkyl)amine, tri-($C_1$ to $C_6$ alkyl)amine, $C_1$ to $C_{10}$ alkanolamine, $C_1$ to $C_6$ alkyl($C_1$ to $C_6$alkanol)amines and di-($C_1$ to $C_6$ alkyl)$C_1$ to $C_6$alkanolamines, wherein the mixture of bases present upon said forming is not a mixture consisting of potassium hydroxide, monoethanolamine and isopropylamine, and wherein the mole ratio of the at least two nitrogen bases:glyphosate acid is in the range of from 0.9:1 to 1.3:1.

2. The method according to claim 1 comprising forming a premix of bases by mixing the bases to form a homogeneous mixture and reacting the premix with glyphosate acid in an aqueous reaction medium.

3. The method according to claim 1 wherein the concentration of glyphosate salts is at least 550 gae/liter.

4. The method according to claim 1 wherein the concentration of the glyphosate is at least 600 gae per liter.

5. The method according to claim 1 wherein the concentration of glyphosate salts is at least 620 gae/liter.

6. The method according to claim 1 wherein the mixture of bases include at least one base other than ammonia and isopropylamine.

7. The method according to claim 1 wherein the nitrogen bases comprise at least two selected from the group consisting of ammonia, mono-($C_1$ to $C_{10}$)alkyl amines, di-($C_1$ to $C_4$) alkyl amines and tri-($C_1$ to $C_4$ alkyl) amines.

8. The method according to claim 1 wherein the nitrogen bases comprise at least two selected from the group consisting of ammonia, methylamine, dimethylamine, diethylamine, isopropylamine, diisopropylamine, triethylamine.

9. The method according to claim 1 wherein the mixture of bases includes at least three bases.

10. The method according to claim 1 comprising loading the aqueous mixture of glyphosate salts into containers of volume in the range of 0.1 to 10000 liters to substantially fill the containers, transporting the filled containers and dispensing the aqueous mixture of glyphosate salts from the containers.

11. The method according to claim 10 wherein the aqueous mixture of glyphosate salts is pumped into the containers.

12. The method according to claim 1 wherein the reaction between the glyphosate acid and nitrogen bases is carried out at a temperature in the range of from 5° C. to 60° C.

13. The method according to claim 1 wherein the method further comprises forming a mixture of at least one further acid herbicide with glyphosate acid and reacting the mixture of the at least two bases with the mixture of glyphosate acid and at least one other acid herbicide.

14. The method according to claim 13 wherein the at least one acid herbicide is selected from the group consisting of dicamba, clopyralid, 2,4-D, MCPA and mecoprop.

15. The method according to claim 1 further comprising addition of a surfactant.

16. The method according to claim 15 wherein the concentration of the surfactant is in the range of from 0.1 to 20% by weight of the aqueous glyphosate concentrate composition.

17. The method according to claim 16 wherein the surfactant comprises one or more selected from the group consisting of quaternary ammonium surfactant; etheramine surfactants; alkylether and amine surfactant combinations; acetylenicdiol and alkyl(poly)glycoside surfactant combinations; lipophilic fatty amine ethoxylate surfactants; alkoxylated amine surfactants; betaine surfactants; alkyl polyglycoside agents; secondary or tertiary alcohol surfactants; silicone copolymer wetting agents and trialkylamine oxide or quaternary amine or trialkylbetaine surfactant combinations; sorbitan fatty acid ester and amine, quaternary ammonium or alkylglycoside surfactant combinations; surfactants derived from alkanethiols; polyoxyalkylenetrisiloxane surfactants; super-wetting agents selected from silicone-based and fluorocarbon-based surfactants; supra-molecular aggregates comprising one or more amphiphilic salts having a glyphosate anion and cation derived by protonation of secondary or tertiary oily amines; alkoxylated primary alcohol surfactants; alkyl polysaccharide derivates; alkyl polyglycoside and ethoxylated alcohol combinations; alkylglucosides; surfactants comprising polyhydroxyhydrocarbyl and amine functionality; alkylglycoside and alkoxylatedalkylamine surfactant combinations; alkyldiaminetetraalkoxylate surfactants; succinic acid derivatives; alkoxylatedamido amines; sugar glycerides; diamine surfactants; widely-bridged alcohol polyethoxylates; water-soluble long-chain hydrocarbyldimethylamine oxides and quaternary ammonium halide combinations; hydroxyalkylammonium adjuvants; polyether diamine surfactants; cationic, anionic, nonionic or zwitterionic silicone adjuvants; organosilicone surfactants and diphenyl oxide sulfonate surfactant combinations; ether phosphate adjuvants; phosphorous surfactant adjuvants; polyglycerol and polyglycerol derivatives; $C_8$-$C_{22}$ sarcosinate or sarcosinate salts; ethoxylated vegetable oils; polyethoxylateddialkylamine surfactants; $C_{10}$-$C_{18}$ alkylpolyglycol ether sulfates; Sucrose &Sorbital Surfactants; Sorbitan Esters; EthoxylatedSaccarhose Esters; Coco Amido Propyl DimethylamineAkyldimethylamines; Phosphated Esters Tallow Amine Surfactants; Trisiloxanes; TEA and MDEA Esterquats; Dimethylethanolamine based Esterquats; Alkyl Polysaccharide; Glucosides; Alkyl Polypentosides (APP); Polyglycerines; EtheramineAlkoxylates; SorbitanMonolaurate; Pine Terpinic compounds; Cocoamineethoxylates; Acrylates & Latex compounds; (Ethoxylated) Oleyl Alcohols; AlkylamineAlkoxylates; EtheramineAlkoxylates/Alkyl Etheramine; Quaternary Ammonium Salts/Ammonium Quaternary Derivatives; Quat Amines; Amine Oxides; Dialkoxylates Amines; Alkyl Alkoxylated Phosphates; AminatedAlkoxylated Alcohols; Dialkoxylated Amines; Carboxylates; Alkylethersulfates; Disodium sulfosuccinates/Succinates; Polyether Amines; Cocoamidopropylbetaines and salts of fatty acids.

18. The method according to claim 1, wherein said forming the mixture and said reacting the mixture with glyphosate acid improves the handling of the resulting aqueous concentrate by reducing the viscosity of the aqueous concentrate as compared to an aqueous concentrate containing the same concentration of glyphosate salt which is formed by either (i) sequential mixing of the at least two nitrogen bases with glyphosate acid or (ii) mixing preformed glyphosate salts of the at least two nitrogen bases.

* * * * *